United States Patent
Coope

(10) Patent No.: US 6,264,703 B1
(45) Date of Patent: Jul. 24, 2001

(54) HAIR COLORING COMPOSITION USING AN INORGANIC PEROXYMONOSULFATE SALT AS AN OXIDATION AGENT

(76) Inventor: Janet Lynn Coope, 71 Aiken St., Apt. L6, Norwalk, CT (US) 06851

(*) Notice: Subject to any disclaimer, the term of this patent is extended or adjusted under 35 U.S.C. 154(b) by 0 days.

(21) Appl. No.: 09/502,084

(22) Filed: Feb. 10, 2000

(51) Int. Cl.$^7$ ...................................... A61K 7/13
(52) U.S. Cl. ................. 8/405; 8/401; 8/406; 8/404; 8/431; 8/435
(58) Field of Search ................. 8/406, 401, 431, 8/404, 405, 435

(56) References Cited

FOREIGN PATENT DOCUMENTS

| 19604274 A1 | 8/1997 | (DE) | A61K/7/135 |
|---|---|---|---|
| WO 97/07776 | 3/1997 | (WO) | A61K/7/135 |
| WO 97/24105 | 7/1997 | (WO) | A61K/7/13 |
| WO 97/24106 | 7/1997 | (WO) | A61K/7/13 |
| WO 97/24107 | 7/1997 | (WO) | A61K/7/13 |
| WO 98/27943 | 7/1998 | (WO) | A61K/7/13 |

OTHER PUBLICATIONS

"Oxone" Monopersulfate Compound, MSDS, 7 pp, Oct. 16, 1996, DuPont Chemicals.

Primary Examiner—Yogendra N. Gupta
Assistant Examiner—Derrick G. Hamlin
(74) Attorney, Agent, or Firm—Carmella A. O'Gorman

(57) ABSTRACT

Inorganic peroxymonosulfate salts used as oxidizing agents for the oxidative dyeing of hair.

8 Claims, 1 Drawing Sheet

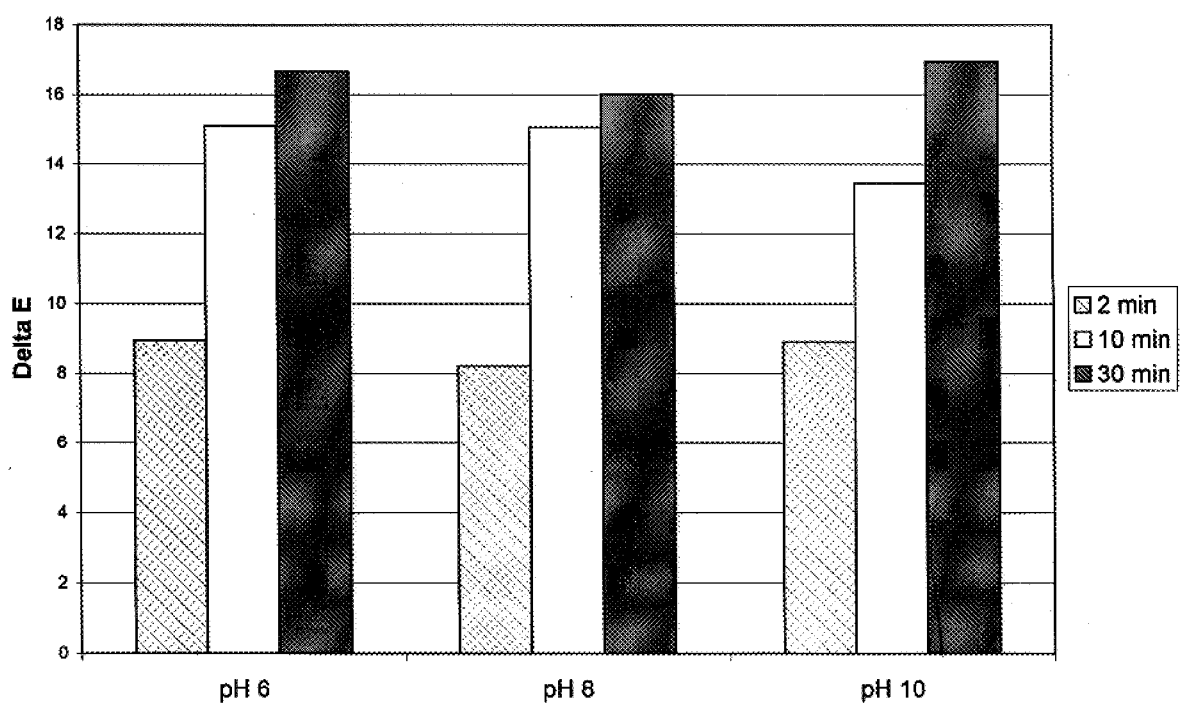
Figure. Color Formation using Oxone

HAIR COLORING COMPOSITION USING AN INORGANIC PEROXYMONOSULFATE SALT AS AN OXIDATION AGENT

FIELD OF THE INVENTION

This invention relates to hair coloring or dyeing compositions and processes for coloring hair. More particularly, this invention relates to the use of a peroxymonosulfate as an oxidizing agent in compositions, systems and processes for the oxidative coloring of hair.

BACKGROUND OF THE INVENTION

Coloration of hair is a procedure practiced from antiquity employing a variety of means. In modern times, the most extensively used method employed to color hair is to color hair by an oxidative dyeing process employing hair coloring systems utilizing one or more oxidative hair coloring agents in combination with one or more oxidizing agents.

Most commonly a peroxy oxidizing agent is used in combination with one or more oxidative hair coloring agents, generally small molecules capable of diffusing into hair and comprising one or more primary intermediates and one or more couplers. In this procedure, a peroxide material, such as hydrogen peroxide, is employed to activate the small molecules of primary intermediates and couplers so that they react to form larger sized complexes in the hair shaft to color the hair in a variety of shades and colors.

Hydrogen peroxide is the most commonly used oxidizing agent employed for oxidative hair dyeing. However, while hydrogen peroxide is the most commonly used oxidizing agent for oxidative coloring of hair, the use of hydrogen peroxide is not without its drawbacks and undesirable characteristics. For example, hydrogen peroxide treatment of hair can solubilize the colored melanin component in hair causing undesirable bleaching of the hair. Moreover, the action of hydrogen peroxide on hair can produce damage to the hair resulting in brittleness and other poor qualities of the hair.

A further drawback in the use of hydrogen peroxide as an oxidizing agent for oxidative dyeing of hair is the requirement for a high pH of above pH 9 for an extended period of time of up to 30 to 60 minutes for the hydrogen peroxide to be in contact with the hair and other dye composition components in order to produce the most effective oxidization of the dye components. While the hydrogen peroxide can be employed at lower pH conditions, oxidation of the dye components and coloration of the hair is generally not as effective.

Additionally, a further drawback is that hydrogen peroxide is a rather unstable liquid requiring special handling and packaging.

In International Application Publication Nos. WO 97/24105, WO 97/24106, WO 97/24107 and WO 98/27943 of the Proctor & Gamble Company, there are proposals for use of organic peroxyacids or precursors therefor as oxidizing agents in hair coloring compositions. However, many of these organic oxidizing agents are liquids that are explosive in nature, not as effective as hydrogen peroxide, and have other drawbacks.

SUMMARY OF THE INVENTION

It is therefore an object of this invention to provide oxidizing agents for use in oxidative hair coloring composition systems and processes that avoid one or more of the foregoing drawbacks. A further object of this invention is to provide oxidizing agents that are solids at ambient temperature and enable handling and packaging thereof without undue special precautions. A still further object of this invention is to provide oxidizing agents for oxidative dyeing of hair that is useable over a wide range of pH and which can cause less damage to hair than hydrogen peroxide, particularly at lower pH values.

According to the present invention, oxidative hair coloring compositions, systems and processes are provided in which an inorganic peroxymonosulfate salt is employed as an oxidizing agent.

DESCRIPTION OF THE DRAWING

The drawing figure charts the Delta E of color formation using an oxidizing agent of this invention at various pH values.

DETAILED DESCRIPTION OF THE INVENTION AND PREFERRED EMBODIMENTS

In accordance with the present invention, an inorganic peroxymonosulfate salt is employed as the oxidizing agent in oxidative hair coloring compositions, systems and processes. The inorganic peroxymonosulfate salt preferably is one of the formula:

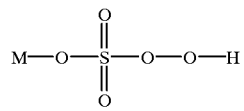

wherein M is a suitable inorganic cation, particularly sodium, potassium and ammonium, preferably potassium. An especially preferred inorganic peroxymonosulfate salt for use in accordance with this invention is potassium peroxymonosulfate available from E. I. duPont de Nemours & Co. under the trademark Oxone®. Oxone® is a triple salt of the formula $2KHSO_5 \cdot KHSO_4 \cdot K_2SO_4$.

The peroxymonosulfate salt oxidizing agent of this invention may be employed in hair coloring compositions and systems of this invention with one or more suitable oxidation hair coloring agents, i.e., one or more suitable primary intermediates and one or more suitable couplers. The resulting dye compositions and systems, when applied to hair, produce dyed hair resistant to wash-out on shampooing and color fastness upon exposure to weather and wear.

For hair coloring compositions of this invention, there may be used one or more suitable primary intermediates and couplers. Suitable primary intermediates include, for example, p-phenylenediamine derivatives such as: 2-methyl-p-phenylenediamine, p-phenylenediamine, 2-chloro-p-phenylenediamine, N-phenyl-p-phenylenediamine, N-(2-methoxyethyl)-p-phenylenediamine, N,N-bis(2-hydroxyethyl)-p-phenylenediamine, 2-hydroxymethyl-p-phenylenediamine, 2-(1-hydroxyethyl)-p-phenylenediamine, 2-(2-hydroxyethyl)-p-phenylenediamine, 4,4'diamino-diphenylamine, 2,6-dimethyl-p-phenylenediamine, 2-isopropyl-p-phenylenediamine, N-(2-hydroxypropyl)-p-phenylenediamine, 2-propyl-p-phenylenediamine, 1,3-bis[(N-hydroxyethyl)-N-(4-aminophenyl)-amino]-2-propanol, 2-methyl-4-dimethylamino-aniline, 2-methoxy-p-phenylenediamine, 2,3-dimethyl-p-phenylenediamine, 2-(1,2-dihydroxyethyl)-p-phenylenediamine and 2-thiophen-2-yl-benzene-1,4-diamine;

p-aminophenol derivatives such as: p-aminophenol, p-methylaminophenol, 3-methyl-4-aminophenol, 2-hydroxymethyl-4-aminophenol, 2-methyl-4-aminophenol, 2-(2'-hydroxyethylaminomethyl)-4-aminophenol, 2-methoxymethyl-4-aminophenol, 5-aminosalicylic acid and 1-(5-amino-2-hydroxyphenyl)-ethane-1,2-diol;

o-aminophenol derivatives such as: o-aminophenol, 2,4-diaminophenol, 5-ethyl-2-aminophenol, 6-methyl-2-aminophenol, 2-ethylamino-p-cresol and 2-amino-5-cetaminophenol and 4-methyl-2-aminophenol; and heterocyclic derivatives such as: 2,4,5,6-tetraaminopyrimidine, 4,5-diamino-1-methylpyrazole, 2-dimethylamino-5-aminopyridine, 1-(2-hydroxyethyl)-4,5-diaminopyrazole, 4-hydroxy-2,5,6-triaminopyrimidine, 2-(2-hydroxyethylamino)-6-methoxy-3-aminopyridine and 3-amino-2-methylamino-6-methoxypyridine.

The primary intermediates can be employed in the form of a free base or in the form of an acid additive salt thereof, such as, for example, as a hydrochloride, a hydrobromide, a sulfate or the like.

Suitable couplers include, for example, phenols, resorcinol and naphthol derivatives such as: 1,7-dihydroxynaphthalene, resorcinol, 4-chlororesorcinol, 1-naphthol, 2-methyl-1-naphthol, 1-acetoxy-2-methyinaphthalene, 1,5-dihydroxynaphthalene, 2,7-dihydroxynaphthalene, hydroquinone, 2-methylresorcinol, 1-hydroxy-6-aminonaphthalene-3-sulfonic acid, 2-isopropyl-5-methylphenol, 1,5-dihydroxy-1,2,3,4-tetrahydronaphthalene, 2-chlororesorcinol, 2,3-dihydroxy-1,4-naphthoquinone and 1-naphthol-4-sulfonic acid, 1,2,3-trihydroxybenzene;

m-phenylenediamines such as: m-phenylenediamine, 2,4-diaminophenoxyethanol, N,N-bis(2-hydroxyethyl)-m-phenylenediamine, 2,6-diaminotoluene, 2-N,N-bis(hydroxyethyl)-2,4-diaminophenetole, 1,3-bis(2,4-diaminophenoxy)propane, 1-hydroxyethyl-2,4-diaminobenzene, 2-amino-4-(2-hydroxyethylamino)anisole, 4-(2-aminoethoxy)-1,3-diaminobenzene, 2,4-diaminophenoxyacetic acid, 4,6-bis(2-hydroxyethoxy)-m-phenylenediamine, 2,4-diamino-5-methylphenetole, 2,4-diamino-5-hydroxyethoxytoluene, 2,4-dimethoxy-1,3-diaminobenzene and 2,6-bis(2-hydroxyethylamino)-toluene, 3-(2,4-diaminophenoxy)-1-propanol;

m-aminophenols such as: m-aminophenol, 2-hydroxy-4-(carbamoylmethylamino)toluene, m-carbamoylmethylaminophenol, 6-hydroxybenzomorpholine, 2-hydroxy-4-aminotoluene, 2-hydroxy-4-(2-hydroxyethylamino)toluene, 4,6-dichloro-m-amino-phenol, 2-methyl-m-aminophenol, 2-chloro-6-methyl-m-aminophenol, 2-(2-hydroxyethoxy)-5-aminophenol, 2-chloro-5-trifluoroethylaminophenol, 4-chloro-6-methyl-m-aminophenol, N-cyclopentyl-3-aminophenol, N-hydroxyethyl-4-methoxy-6-methyl-m-aminophenol and 5-amino-4-methoxy-2-methylphenol; and heterocyclic derivatives such as: 1-phenyl-3-methyl-5-pyrazolone, 6-methoxy-8-aminoquinoline, 2,6-dihydroxy-4-methylpyridine, 5-hydroxy-1,4-benzodioxane, 3,4-methylenedioxyphenol, 4-(2-hydroxyethylamino)-1,2-methylene-dioxybenzene, 2,6-dihydroxy-3,4-dimethylpyridine, 5-chloro-2,3-dihydroxypyridine, 3,5-diamino-2,6-dimethoxypyridine, 3,4-methylene-dioxyaniline, 2,6-bis(2-hydroxyethoxy)-3,5-diaminopyridine, 4-hydroxyindole, 3-amino-5-hydroxy-2,6-dimethoxypyridine, 5,6-dihydroxyindole, 7-hydroxyindole, 5-hydroxyindole, 2-bromo-4,5-methylenedioxyphenol, 6-hydroxyindole, 2-amino-3-hydroxypyridine, 2,6-diaminopyridine, 5-(3,5-diamino-2-pyridyloxy)-1,3-dihydroxypentane, 3-(3,5-diamino-2-pyridyloxy)-2-hydroxypropanol and isatin.

Preferred primary intermediates include:

p-phenylenediamine derivatives such as: 2-methyl-p-phenylenediamine, p-phenylenediamine, N-(2-methoxyethyl)-p-phenylenediamine, N,N-bis(2-hydroxyethyl)-p-phenylenediamine, 2-(1-hydroxyethyl)-p-phenylenediamine, 2-(2-hydroxyethyl)-p-phenylenediamine, and 2-(1,2-dihydroxyethyl)-p-phenylenediamine;

p-aminophenol derivatives such as: p-aminophenol, p-methylaminophenol, 3-methyl-4-aminophenol, 2-methoxymethyl-4-aminophenol and 1-(5-amino-2-hydroxyphenyl)-ethane-1,2-diol;

o-aminophenol derivatives such as: o-aminophenol, 2-ethylamino-pcresol, 5-methyl-2-aminophenol, 6-methyl-2-aminophenol and 2-amino-5-acetaminophenol, 4-methyl-2-aminophenol; and heterocyclic derivatives such as: 2,4,5,6-tetraaminopyrimidine 4,5-diamino-1-methylpyrazole, 1-(2-hydroxyethyl)-4,5-diaminopyrazole, and 2-dimethylamino-5-aminopyridine.

Preferred couplers include:

phenols, resorcinol and naphthol derivatives such as: 2-methyl-1-naphthol, 1-acetoxy-2-methylnaphthalene, 1,7-dihydroxynaphthalene, resorcinol, 4-chlororesorcinol, 1-naphthol, 1,5-dihydroxynaphthalene, 2,7-dihydroxynaphthalene, hydroquinone, 2-methylresorcinol and 2-isopropyl-5-methylphenol;

m-phenylenediamines such as: m-phenylenediamine, 2,4-diaminophenoxyethanol, 1,3-bis(2,4-diaminophenoxy)propane, 2-amino-4-(2-hydroxyethylamino)anisole and 4,6-bis(2-hydroxyethoxy)-m-phenylenediamine, 3-(2,4-diaminophenoxy)-1-propanol;

m-aminophenols such as: m-aminophenol, 6-hydroxybenzomorpholine, 2-hydroxy-4-aminotoluene, 2-hydroxy-4-(2-hydroxyethylamino)toluene and 2-methyl-maminophenol; and heterocyclic derivatives such as: 1-phenyl-3-methyl-5-pyrazolone, 3,4-methylenedioxyphenol, 3,4-methylenedioxyaniline, 4-hydroxyindole, 5,6-dihydroxyindole, 7-hydroxyindole, 5-hydroxyindole, 6-hydroxyindole, isatin, 2,6-diaminopyridine and 2-amino-3-hydroxypyridine.

Most preferred primary intermediates include:

p-phenylenediamine derivatives such as: 2-methyl-p-phenylenediamine, p-phenylenediamine, N,N-bis(2-hydroxyethyl)-p-phenylenediamine, 2-(1-hydroxyethyl)-p-phenylenediamine and 2-(2-hydroxyethyl)-p-phenylenediamine;

p-aminophenol derivatives such as: p-aminophenol, p-methylaminophenol, 3-methyl-4-aminophenol and 1-(5-amino-2-hydroxyphenyl)-ethane-1,2-diol;

o-amino derivatives such as: o-aminophenol, 2-ethylamino-p-cresol, 5-methyl-2-aminophenol, 6-methyl-2-aminophenol and 2-amino-5-acetaminophenol; and heterocyclic derivatives such as: 2,4,5,6-tetraaminopyrimidine and 1-(2-hydroxyethyl)-4,5-diaminopyrazole.

Most preferred couplers include:

phenols, resorcinol and naphthol derivatives such as: 2-methyl-1-naphthol, 1-acetoxy-2-methyinaphthalene, resorcinol, 4-chlororesorcinol, 1-naphthol and 2-methylresorcinol;

m-phenylenediamines such as: 2,4-diaminophenoxyethanol, 2-amino-4-(2-hydroxyethylamino)anisole and 4,6-bis(2-hydroxyethoxy)-m-phenylenediamine and 3-(2,4-diaminophenoxy)-1-propanol;

m-aminophenols such as: m-aminophenol, 6-hydroxybenzomorpholine, 2-hydroxy-4-aminotoluene, 2-hydroxy-4-(2-hydroxyethylamino)toluene and 2-methyl-m-aminophenol; and heterocyclic derivatives such as: 1-phenyl-3-methyl-5-pyrazolone, 2-amino-3-hydroxypyridine and 6-hydroxyindole.

The hair coloring compositions of this invention will generally contain one or more couplers in an effective coloring amount, generally in an amount of from about 0.01 to about 2.5 weight percent. The primary intermediate(s) will generally be present in an amount of from about 0.01 to about 3.5 weight percent. The molar ratio of primary intermediate to coupler will generally range from about 5:1 to about 1:5 and be employed in any suitable carrier or vehicle, generally an aqueous or hydroalcoholic solution, preferably an aqueous solution. The carrier or vehicle will generally comprise up to about 40 weight percent.

The hair coloring compositions of this invention may contain one or more cationic, anionic or amphoteric surface active agents perfumes, antioxidants, sequestering agents, thickening agents, alkalizing or acidifying agents, and other dyeing agents.

In general, a first composition of primary intermediate(s) and coupler(s) is prepared and then, at the time of use, is admixed with the inorganic peroxymonosulfate salt until an essentially homogenous composition is obtained. The resulting composition is applied to the hair to be dyed and permitted to remain in contact with the hair for a dyeing effective amount of time, generally for a period of from about 2 to 45, preferably about 2 to 30, minutes, after which the hair is rinsed, shampooed and dried.

The invention is illustrated by, but not limited to, the following examples.

EXAMPLES 1 to 3

A hair dye base was prepared from the following components.

| Hair Dye Base Formilation | |
|---|---|
| Component | wt (g) |
| p-phenylenediamine | 2.4 |
| p-aminophenol | 0.9 |
| m-aminophenol | 0.6 |
| 2-amino3-hydroxypyridine | 0.6 |
| EDTA | 1.0 |
| sodium sulfite | 1.0 |
| water | balance to 800 g |

Oxidant mixtures were prepared as follows. 50 mL of the aforementioned Hair Dye Base Formulation was added to a powder composition containing 1.0 g Oxone® plus one of the following buffering agents to produce an Oxidant Mixture of the indicated pH value.

Example 1: pH 6 4.9 g trisodium citrate
Example 2: pH 8 4.2 g sodium bicarbonate
Example 3: pH 10 4.2 g sodium carbonate monohydrate and 0.9 g sodium bicarbonate The OXONE® employed was obtained from E. I. duPont. Iodometric titration thereof gave an activity of 4.55% active oxygen. Thus, 2 wt % OXONE® is 0.091% active oxygen in the Oxidant Mixtures.

For hair dyeing, three tresses of blended gray hair (1.5 g each) were placed in a jar containing one of the Oxidant Mixtures. After sitting at ambient temperature for the specified time, the tresses were removed from the formulation and rinsed with tap water. The tresses were then read on a Minolta Reflectometer.

The coloration results in FIG. 1 show that color formation is substantially independent of pH. The color obtained is light brown. Table 1 shows representative color scale values for each Oxidative Mixture after 30 minutes of contact with the hair tresses.

A method has been developed using a Minolta Chroma Meter CR-200, which uses reflected light from a surface and gives results in terms of the CIE (International Commission on Illumination) tristimulus values. These values are subsequently transformed mathematically into the L* a* b* color space, wherein the magnitudes of changes in hue and intensity of color correspond closely with those perceived by the human eye.

L*, being achromatic, ranges from black (L*=0) to white (L*=100); this term is called "metric lightness" and is a measure of how light or dark a color is, relative to a matching shade of gray. Hue is measured in terms of the chromaticity coordinates a* and b*, where a* indicates redness (a*>0) and b* indicates yellowness (b*>0). The values of a* and b* can be plotted with a* as the x-axis and b* as the y axis, to give quantitative color information: "metric chroma" is the length of a line from the origin (a*=0, b*=0) to the point of a sample reading, while metric hue angle, is the angle between the a* axis and the metric chroma line. Metric chroma indicates the strength of a color response (i.e., the extent to which a color differs from its matching shade of gray). Metric hue angle quantifies hue in degrees, with larger values indicating more yellow hues and smaller values indicating more red (or less yellow) hues.

The meter can be used to measure a base line tone as well as residual color left.

TABLE 1

CIE L*a*b readings for Oxone ® Oxidant Mixtures after 30 minutes

| | L* | a* | b* | ΔE |
|---|---|---|---|---|
| initial gray | 36.5 | 0.4 | 5.7 | — |
| hair dyed at pH 6 | 20.0 | 2.5 | 5.1 | 16.7 |
| hair dyed at pH 8 | 20.8 | 3.4 | 5.6 | 16.0 |
| hair dyed at pH 10 | 19.8 | 2.9 | 5.1 | 17.0 |

$\Delta E = \sqrt{(\Delta L^*)^2 + (\Delta a^*)^2 + (\Delta b^*)^2}$

EXAMPLE 4

Assessment of hair damage during oxidative dyeing for 30 minutes with the Oxidative Mixtures of Examples 1 to 3 and a comparative dyeing mixture using a standard hydrogen peroxide developer (0.88 M) were carried out by measuring water retention of the dyed hair according to a method described by E. I. Valko and C. Barnett in J. Soc. Cosmet. Chem., 3, 108 (1952). Lower water retention is an indication of less damage to the hair. Table 2 shows that damage with the Oxone® Oxidant Mixtures of Examples 1 to 3 is comparable to the standard hydrogen peroxide at higher pH (pH 10) but less at lower pH values (pH 8 and 6) than the standard hydrogen peroxide.

TABLE 2

| Oxidant | pH | % water retention |
|---|---|---|
| Oxone | 6 | 30.3 |
| Oxone | 8 | 35.0 |
| Oxone | 10 | 36.2 |
| Hydrogen peroxide (0.88 M) | 10 | 36.9 |

With the foregoing description of the invention, those skilled in the art will appreciate that modifications may be made to the invention without departing from the spirit thereof. Therefore, it is not intended that the scope of the invention be limited to the specific embodiments illustrated and described.

I claim:

1. A hair coloring composition comprising one or more oxidative hair coloring agents, an inorganic peroxymonosulfate of the formula:

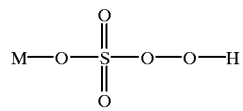

wherein M is selected from the group consisting of sodium, potassium and ammonium.

2. A hair coloring composition according to claim 1 wherein M is potassium.

3. A hair coloring composition according to claim 2 wherein the potassium peroxymonosulfate is present as a triple salt of the formula: $2KHSO_5 \cdot KHSO_4 \cdot K_2SO_4$.

4. A hair coloring composition according to claim 1 wherein the one or more oxidative hair coloring agents comprises.

5. A hair coloring system according to claim 4 wherein the at least one primary intermediate is selected from the group consisting of: 2-methyl-p-phenylenediamine, p-phenylenediamine, N,N-bis(2-hydroxyethyl)-p-phenylenediamine, 2-(1-hydroxyethyl)-p-phenylenediamine, 2-(2-hydroxyethyl)-p-phenylenediamine, p-aminophenol, p-methylaminophenol, 3-methyl-4-aminophenol, 1-(5-amino-2-hydroxyphenyl)-ethane-1,2-diol, o-aminophenol, 2-ethylamino-p-cresol, 5-methyl-2-aminophenol, 6-methyl-2-aminophenol 2-amino-5-acetaminophenol, 2,4,5,6-tetraaminopyrimidine and 1-(2-hydroxyethyl)-4,5-diaminopyrazole.

6. A hair coloring system according to claim 4 wherein the at least one coupler is selected from the group consisting of: 2-methyl-1-naphthol, 1-acetoxy-2-methylnaphthalene, resorcinol, 4-chlororesorcinol, 1-naphthol, 2-methylresorcinol, 2,4-diaminophenoxyethanol, 2-amino-4-(2-hydroxyethylamino)anisole and 4,6-bis(2-hydroxyethoxy)-m-phenylenediamine, 3-(2,4-diaminophenoxy)-1-propanol, m-aminophenol, 6-hydroxybenzomorpholine, 2-hydroxy-4-aminotoluene, 2-hydroxy-4-(2-hydroxyethylamino)toluene, 2-methyl-m-aminophenol, and 1-phenyl-3-methyl-5-pyrazolone, 2-amino-3-hydroxypyridine and 6-hydroxyindole.

7. A hair coloring composition according to claim 4 wherein the at least one primary intermediate is selected from the group consisting of p-phenylenediamine and paminophenol, and the at least one coupler is selected from the group consisting of m-aminophenol and 2-amino-3-hydroxypyridine.

8. A process for the oxidative coloring of human hair comprising applying a dyeing effective amount of a hair coloring composition of claim 1 to the hair and permitting the composition to contact the hair for a dyeing effective period of time, and then rinsing, shampooing and drying the hair.

* * * * *